US011911765B2

(12) United States Patent
Yen et al.

(10) Patent No.: US 11,911,765 B2
(45) Date of Patent: Feb. 27, 2024

(54) REAGENT EXCHANGE IN AN INSTRUMENT (71) Applicant: ILLUMINA, INC., San Diego, CA (US)

(72) Inventors: Tony Yen, San Diego, CA (US); Eric Stava, San Diego, CA (US); Rajagopal Panchapakesan, Escondido, CA (US)

(73) Assignee: ILLUMINA, INC., San Diego, CA (US)

( * ) Notice: Subject to any disclaimer, the term of this patent is extended or adjusted under 35 U.S.C. 154(b) by 675 days.

(21) Appl. No.: 16/902,826

(22) Filed: Jun. 16, 2020

(65) Prior Publication Data

US 2020/0398278 A1    Dec. 24, 2020

Related U.S. Application Data (60) Provisional application No. 62/863,444, filed on Jun. 19, 2019.

(51) Int. Cl.
  *B01L 3/00*   (2006.01)
  *C12Q 1/6869*  (2018.01)
  *G06T 7/00*   (2017.01)

(52) U.S. Cl.
  CPC ........... *B01L 3/527* (2013.01); *C12Q 1/6869* (2013.01); *G06T 7/0012* (2013.01);
  (Continued)

(58) Field of Classification Search
  CPC ............ B01L 3/527; B01L 2300/0861; B01L 2300/0877; B01L 2200/027;
  (Continued)

(56) References Cited

U.S. PATENT DOCUMENTS 7,835,871 B2    11/2010   Kain et al.
2013/0184162 A1  7/2013   Bridgham et al.
(Continued)

FOREIGN PATENT DOCUMENTS

EP    3373174 P    9/2018
WO    2017087823   5/2017
(Continued)

OTHER PUBLICATIONS

Cacho et al, A Comparison of Base-calling Algorithms for Illumina Sequencing Technology, 2016, Briefings in Bioinformatics, 17(5), 2016, 786-795. (Year: 2016).*
(Continued)

*Primary Examiner* — Narayan K Bhat
(74) *Attorney, Agent, or Firm* — Heslin Rothenberg Farley & Mesiti PC (57) ABSTRACT

A method includes flowing an incorporation reagent through a reagent management system and a flow cell of an instrument. The flow cell having a first polynucleotide positioned therein. The incorporation reagent adding a first base onto a sequence of bases. The sequence of bases includes a second polynucleotide complementary to the first polynucleotide. An image of an identification signal emanating from the first base is captured after the first base has been added onto the second polynucleotide. A cleavage reagent is flowed through the reagent management system and flow cell to remove a first terminator from the first base in order to enable a subsequent base in the sequence of bases to be added to the second polynucleotide. A buffer reagent is flowed through the reagent management system and flow cell in a plurality of cycles of consecutive forward and reverse flow directions.

20 Claims, 8 Drawing Sheets

(52) U.S. Cl.
CPC ............... *B01L 2300/0861* (2013.01); *B01L 2300/0877* (2013.01); *G06T 2207/30024* (2013.01)

(58) Field of Classification Search
CPC ....... B01L 2300/0819; B01L 3/502715; B01L 3/50273; B01L 2200/141; B01L 2200/16; B01L 2400/0644; B01L 2200/04; C12Q 1/6869; C12Q 2565/629; C12Q 2563/107; G06T 7/0012; G06T 2207/30024
See application file for complete search history.

(56) References Cited

U.S. PATENT DOCUMENTS

| | | |
|---|---|---|
| 2015/0079585 A1 | 3/2015 | Wimberger-Friedl et al. |
| 2016/0068902 A1 | 3/2016 | Farinas |
| 2016/0168633 A1 | 6/2016 | Previte et al. |
| 2018/0187252 A1 | 7/2018 | Hunter et al. |
| 2018/0188279 A1 | 7/2018 | Whitacre et al. |

FOREIGN PATENT DOCUMENTS

| | | |
|---|---|---|
| WO | 2018187201 | 10/2018 |
| WO | 2019221913 | 11/2019 |

OTHER PUBLICATIONS

Stephen P. Scuderi, One Page Invention Summary, dated May 14, 2019. Albany, NY.

* cited by examiner

Total Fluidic Consumption Held at 48 (µL)

190 ⟶

| Total Sweep Volume (µL) / Total Fluidic Consumption (µL) | Total Sweep Volume (µL) | First Forward Flow Volume (µL) | Second Reverse Flow Volume (µL) | # of Cycles | Third Forward Flow Volume (µL) | |
|---|---|---|---|---|---|---|
| 48/48 = 1 | 48 | 0 | 0 | 0 | 48 | —190-1 |
| 100/48 = 2.08 | 100 | 25 | 13 | 2 | 24 | —190-2 |
| 200/48 = 4.16 | 200 | 25 | 19 | 4 | 24 | —190-3 |
| 300/48 = 6.25 | 300 | 25 | 21 | 6 | 24 | —190-4 |
| 444/48 = 9.25 | 444 | 25 | 22 | 9 | 21 | —190-5 |
| 600/48 = 12.5 | 600 | 25 | 23 | 12 | 24 | —190-6 |
| 1200/48 = 25 | 1200 | 25 | 24 | 24 | 24 | —190-7 |

REAGENT EXCHANGE IN AN INSTRUMENT

CROSS-REFERENCE TO RELATED APPLICATION

This Patent Application claims priority to U.S. Provisional Patent Application No. 62/863,444, filed Jun. 19, 2019, and entitled Reagent Exchange In An Instrument. The entire contents of the aforementioned application is hereby incorporated herein by reference.

BACKGROUND

Instruments utilized in the performance of methods to determine the order of nucleotides in a polynucleotide, may include a reagent management system (RMS) in fluid communication with a flow cell. The RMS is capable of storing, selecting and sequentially flowing a plurality of reagents through a flow channel of the flow cell.

Such methods may include multiple cycles of a sequence of selected reagents that are routed through the flow channel of the flow cell in order to perform various controlled chemical reactions on clusters of cloned first polynucleotides positioned in the flow channel of the flow cell. The chemical reactions enable tagged nucleotides to form base pairs, one base pair at a time, with the sequence o bases of the first polynucleotides. Once paired, the tags are excited to emit an identification signal which identifies the base pair. Each tagged polynucleotide adds to a growing complementary second polynucleotide strand that is double stranded with the first polynucleotide in the flow cell.

Accordingly, the complementary second polynucleotide strands may be built up, one base at a time, to determine the sequence of bases in the cluster of first polynucleotides. The greater the number of known nucleotides in the complementary second polynucleotide strands that can be built up (i.e., the longer the second polynucleotide strand length becomes), the more data can be provided regarding the order of nucleotides in the cluster of first polynucleotides and the faster the overall analysis becomes.

However, if reagent exchange between the reagent flows is not sufficient, then cross contamination between reagents can occur. Accordingly, there is a need for instruments and methods to determine the order of nucleotides in polynucleotides, which have improved reagent exchange between reagent flows.

BRIEF DESCRIPTION

The present disclosure offers advantages by providing an instrument operable to perform a method of determining the order of nucleotides in a polynucleotide in accordance with one or more aspects of the present disclosure. The method includes a wash phase, wherein when flowing a buffer reagent through a reagent management system and a flow cell of an instrument, the total sweep volume of the buffer reagent is greater than the total fluidic consumption of the buffer reagent. Further, the ratio of the total sweep volume to total fluidic consumption may be as high as 6, 10 or more. The method enhances reagent exchange over other methods, wherein the total sweep volume to total fluidic consumption is 1. As such, pre-phasing is reduced and the length of polynucleotides that may be grown is increased relative to such other methods.

A method in accordance with one or more aspects of the present disclosure includes flowing an incorporation reagent through a reagent management system and a flow cell of an instrument. The flow cell having a first polynucleotide positioned therein. The incorporation reagent adding a first base onto a sequence of bases. The sequence of bases includes a second polynucleotide complementary to the first polynucleotide. An image of an identification signal emanating from the first base is captured after the first base has been added onto the second polynucleotide. A cleavage reagent is flowed through the reagent management system and flow cell to remove a first terminator from the first base in order to enable a subsequent base in the sequence of bases to be added to the second polynucleotide. A buffer reagent is flowed through the reagent management system and flow cell in a plurality of cycles of consecutive forward and reverse flow directions to wash the cleavage reagent from the reagent management system and flow cell.

In some examples of the method, the plurality of cycles comprises 4 or more cycles.

In some examples of the method, the plurality of cycles comprises 12 or more cycles.

In some examples of the method, the reagent management system and the flow cell are positioned in a cartridge of the instrument, the cartridge being removably insertable into the instrument.

In some examples of the method, the incorporation reagent, the cleavage reagent and the buffer reagent are stored in reagent wells of the reagent management system, the reagent wells configured to store a finite total volume of each reagent.

In some examples of the method, flowing the buffer reagent comprises: flowing a first forward flow volume of the buffer reagent in the forward flow direction of each cycle of the plurality of cycles; and flowing a second reverse flow volume of the buffer reagent in the reverse flow direction of each cycle of the plurality of cycles, the first forward flow volume being greater than the second reverse flow volume.

In some examples of the method, the forward flow volume is greater than the reverse flow volume by about 3% or more.

In some examples of the method, flowing the buffer reagent comprises: an incubation period of substantially no flow of buffer reagent through the reagent management system and flow cell for about 10 seconds or more after the last cycle of the plurality of cycles; and flowing a third forward flow volume of the buffer reagent in the forward flow direction after the incubation period.

In some examples of the method, total sweep volume of the buffer reagent, during the flowing the buffer reagent, is substantially determined by the formula $((1^{st} FFV + 2^{nd} RFV) * N) + 3^{rd} FFV$, wherein:

$1^{st}$ FFV is the first forward flow volume,
$2^{nd}$ RFV is the second reverse flow volume,
N is the total number of cycles in the plurality of cycles, and
$3^{rd}$ FFV is the third forward flow volume.

In some examples of the method, total fluidic consumption of the buffer reagent, during the flowing the buffer reagent, is substantially determined by the formula $((1^{st} FFV + 2^{nd} RFV) * N) + 3^{rd} FFV$.

In some examples of the method, the ratio of the total sweep volume of the buffer reagent to the total fluidic consumption of the buffer reagent is equal to or greater than about 6.

In some examples of the method, the flowing in a forward flow direction and the flowing in a reverse flow direction are separated by a delay time of about 1 second or less for each cycle of the plurality of cycles of forward and reverse flow directions.

In some examples of the method, the flowing in a forward flow direction and flowing in a reverse flow direction is separated by a delay time of about 200 milliseconds or less for each cycle of the plurality of cycles of forward and reverse flow directions.

In some examples of the method, each cycle of the plurality of cycles of forward and reverse flow directions is separated by a delay time of about 200 milliseconds or less.

Any of the examples of the method can be implemented in any suitable combination to achieve the advantages described herein.

An instrument in accordance with one or more aspects of the present disclosure includes a reagent management system operable to be positioned in the instrument. The reagent management system includes a plurality of reagent wells. The reagent wells have at least a first, a second and a third reagent well configured to contain an incorporation reagent, a cleavage reagent and a buffer reagent positioned respectively therein. The reagent management system is operable to select a flow of reagent from one of the plurality of reagent wells. A flow cell is operable to be positioned in the instrument. The flow cell includes a flow channel in fluid communication with the reagent management system. The flow channel is operable to route the flow of reagent over a first polynucleotide positioned in the flow channel. The instrument is operable to:

flow the incorporation reagent, through the reagent management system and flow cell, to add a first base onto a sequence of bases, the sequence of bases comprising a second polynucleotide complementary to the first polynucleotide;

capture an image, of an identification signal emanating from the first base, after the first base has been added onto the second polynucleotide;

flow the cleavage reagent, through the reagent management system and flow cell, to remove a first terminator from the first base in order to enable a subsequent base in the sequence of bases to be added to the second polynucleotide; and flow the buffer reagent, through the reagent management system and flow cell in a plurality of cycles of consecutive forward and reverse flow directions to wash the cleavage reagent from the reagent management system and flow cell.

In some examples, the instrument comprises a cartridge operable to contain the reagent management system and the flow cell, wherein the incorporation reagent, the cleavage reagent and the buffer reagent are stored in reagent wells of the reagent management system, the reagent wells configured to store a finite total volume of each reagent.

In some examples, the instrument is operable to flow the buffer reagent through the reagent management system and flow cell in a plurality of 4 or more cycles of consecutive forward and reverse flow directions.

In some examples, the instrument is operable to flow the buffer reagent such that:

a first volume of the buffer reagent is flowed in the forward flow direction of each cycle of the plurality of cycles;

a second volume of the buffer reagent is flowed in the reverse flow direction of each cycle of the plurality of cycles, the first volume being greater than the second volume;

an incubation period of substantially no flow of the buffer reagent through the reagent management system and flow cell is imposed for about 10 seconds or more after the last cycle of the plurality of cycles; and a third forward flow volume of the buffer reagent is flowed in the forward flow direction after the incubation period.

In some examples, the instrument is operable to flow the buffer reagent such that:

a total sweep volume of the buffer reagent is substantially determined by the formula $((1^{st}\ FFV + 2^{nd}\ RFV) * N) + 3^{rd}\ FFV$ wherein:

$1^{st}$ FFV is the first forward flow volume, $2^{nd}$ RFV is the second reverse flow volume, N is the total number of cycles in the plurality of cycles, and $3^{rd}$ FFV is the third forward flow volume;

a total fluidic consumption of the buffer reagent is substantially determined by the formula $((1^{st}\ FFV - 2^{nd}\ RFV) * N) + 3^{rd}\ FFV$; and wherein the ratio of the total sweep volume of the buffer reagent to the total fluidic consumption of the buffer reagent is equal to or greater than about 6.

In some examples, the instrument is operable to flow the buffer reagent such that the flowing in a forward flow direction and flowing in a reverse flow direction is separated by a delay time of about 200 millisecond or less for each cycle of the plurality of cycles of forward and reverse flow directions.

Any of the examples of the instruments can be implemented in any suitable combination to achieve the advantages described herein.

It should be appreciated that all combinations of the foregoing aspects, including the methods and instruments, and additional concepts discussed in greater detail below (provided such concepts are not mutually inconsistent) are contemplated as being part of the inventive subject matter disclosed herein.

These and other objects, features and advantages of this disclosure will become apparent from the following detailed description of the various aspects of the disclosure taken in conjunction with the accompanying drawings.

DRAWINGS

The disclosure will be more fully understood from the following detailed description taken in conjunction with the accompanying drawings, in which.

DETAILED DESCRIPTION

Certain examples will now be described to provide an overall understanding of the principles of the structure, function, manufacture, and use of the methods, systems, and devices disclosed herein. One or more examples are illustrated in the accompanying drawings. Those skilled in the art will understand that the methods, systems, and devices specifically described herein and illustrated in the accompanying drawings are non-limiting examples and that the scope of the present disclosure is defined solely by the claims. The features illustrated or described in connection with one example may be combined with the features of other examples. Such modifications and variations are intended to be included within the scope of the present disclosure.

The terms "substantially", "approximately", "about", "relatively," or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Figure 1:
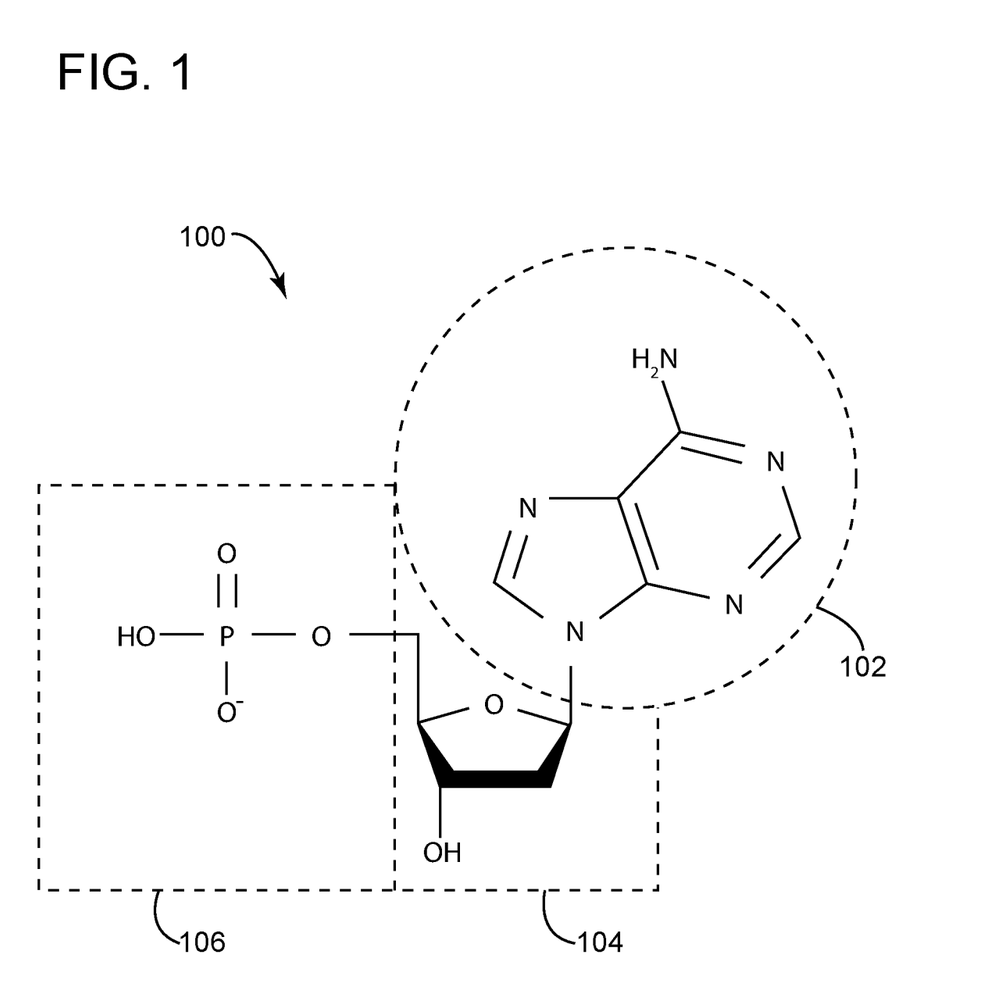
FIG. 1 depicts a simplified example of the chemical structure of a nucleotide according to aspects disclosed herein.

Referring to FIG. 1, a simplified example of the chemical structure of a nucleotide 100 according to aspects disclosed herein is depicted. Nucleotide 100 is composed of the following three sub-unit molecules: a nitrogenous base 102 (also known as a nucleobase or a base), a five-carbon sugar 104 (such as ribose or deoxyribose) and at least one phosphate group 106. Multiple nucleotides that are connected together are known as polynucleotides. First and second polynucleotides 108 and 110, best seen on FIG. 2, are examples of such polynucleotides.

The nitrogenous base 102 of nucleotide 100 may be one of the following five types: adenine (A), guanine (G), cytosine (C), thymine (T) and uracil (U). Each type of base 102 will pair (i.e., chemically attach) to only one other base type to form a complementary base pair in two complementary double strands of polynucleotides, such as the complementary double stranded polynucleotide 112 shown in FIG. 2.

Complementary, as used herein, refers to the pairing of a first base of a first nucleotide with the specific second base of a second nucleotide that may chemically attach to it. The second base (and its associated nucleotide) is considered herein complementary to the first base (and its associated nucleotide). For example: adenine-thymine (A-T) and guanine-cytosine (G-C) are complementary base pairs that may connect complementary double polynucleotide strands of deoxyribonucleic acid (DNA). Also, adenine-uracil (A-U) and guanine-cytosine (G-C) are complementary base pairs that may connect complementary double polynucleotide strands of ribonucleic acid (RNA).

Figure 2:
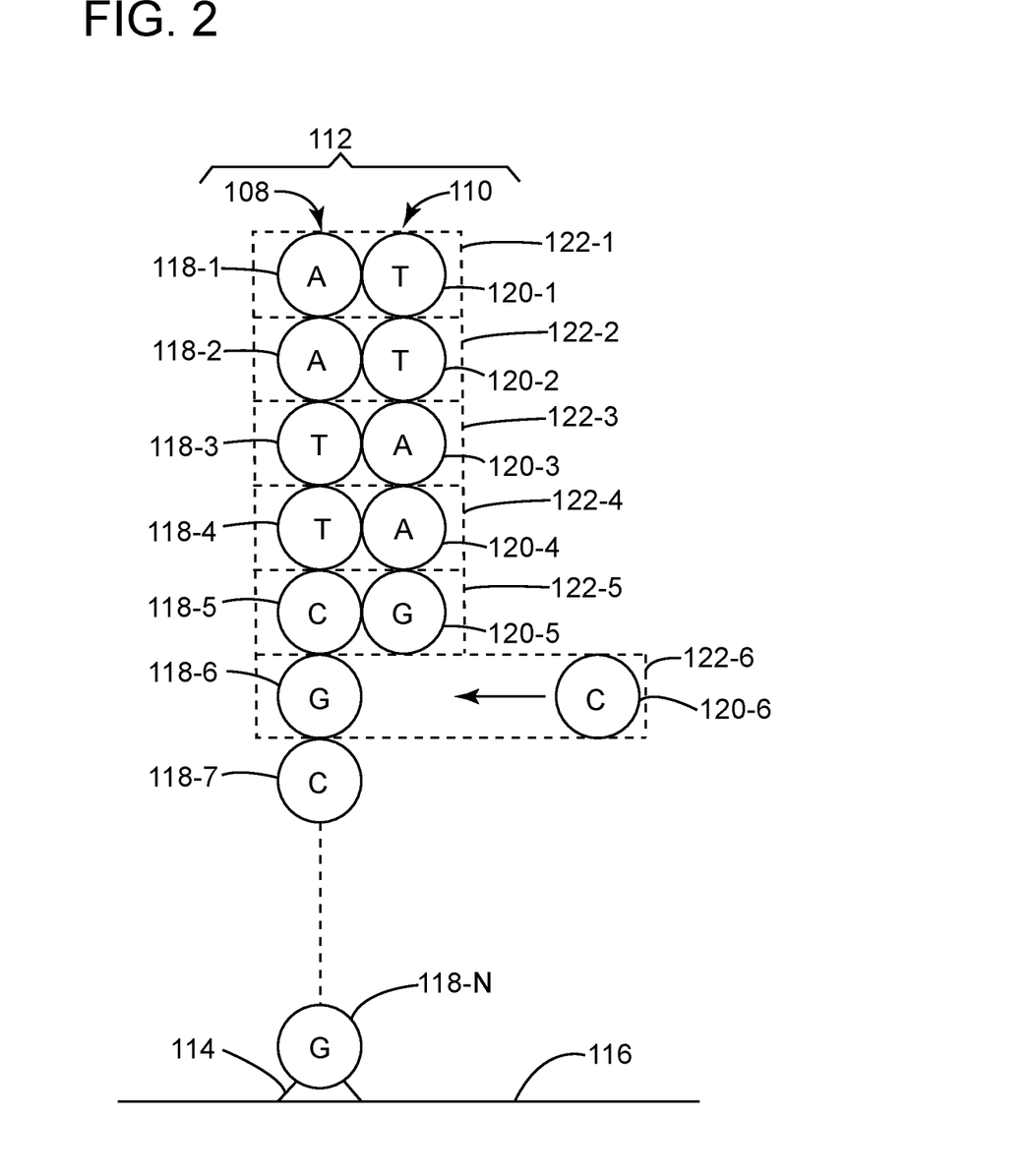
FIG. 2 depicts a simplified example of a first polynucleotide and a growing complementary second polynucleotide according to aspects described herein.

Referring to FIG. 2, a simplified example of a first polynucleotide 108 and a growing complementary second polynucleotide 110 according to aspects described herein is depicted. The first and second polynucleotides 108, 110 are connected together to form a double stranded polynucleotide 112.

Figure 7:
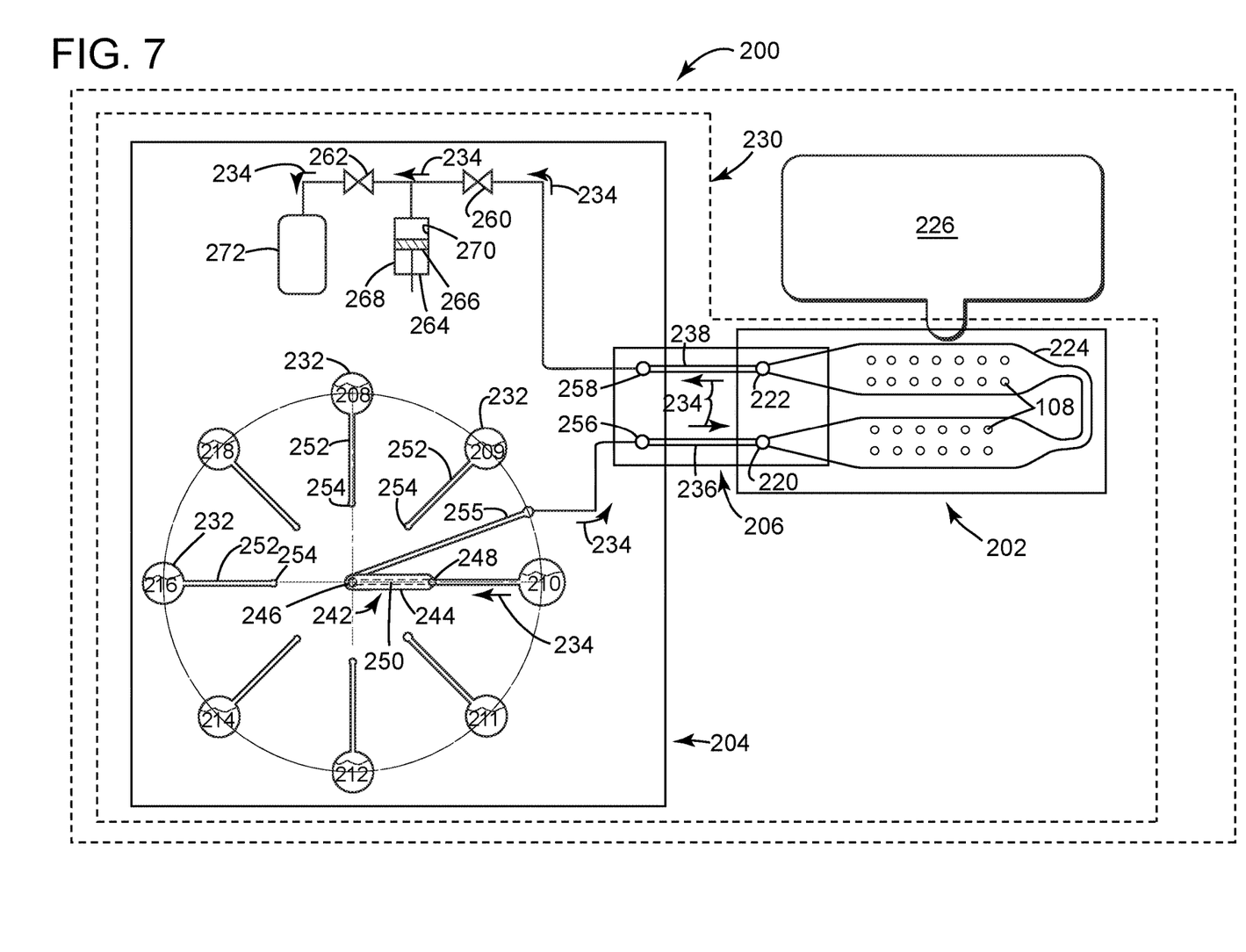
FIG. 7 depicts an example of a schematic diagram of an instrument according to aspects disclosed herein.

The first polynucleotide 108 is chemically anchored 114 to a floor 116 of a flow channel 224 of a flow cell 202 (best seen in FIG. 7). The first polynucleotide 108 includes nucleotides 118-1 through 118-N, wherein N represents the total number of nucleotides 118 in the first polynucleotide 108 and is also indicative of the length of the first polynucleotide 108. The specific type of nitrogenous base associated with each nucleotide 118 is identified by the circled letters A, G, C or T, which represent the base types adenine, guanine, cytosine and thymine respectively. The first polynucleotide 108 may be one of many clusters of cloned identical first polynucleotides 108 anchored to the floor 116 of the flow channel 224.

The second polynucleotide 110 includes at least nucleotides 120-1 through 120-6. Again, the specific type of nitrogenous base associated with each nucleotide 120 is identified by the circled letters A, G, C or T. Each nucleotide 120 includes a chemical tag (such as a florescent tag) which, when excited (for example by an excitation light), will emit an identification signal (such as a florescent light) which will identify the specific base of the nucleotide 120.

The bases of the nucleotides 120 can only attach to a complementary base of the nucleotides 118 to form a series of complementary base pairs 122-1 through 122-6. The base pairs 122 and their associated nucleotide 118, 120 form the double stranded polynucleotide 112.

An instrument, such as instrument 200, utilized in the performance of methods to determine the order of nucleotides 118-1 through 118-N in the first polynucleotide 108, may include a reagent management system 204 in fluid communication with a flow cell 202 (best seen in FIG. 7). The reagent management system is capable of storing, selecting and sequentially flowing a plurality of reagents through the flow channel 224 of the flow cell 202. The reagent management system and/or flow cell may, or may not, be located in a removably insertable cartridge 230 (best seen in FIG. 7) of the instrument.

As will be explained in greater detail herein, such methods may include multiple cycles of a sequence of selected reagents 208-218 (best seen in FIG. 7) that are routed through the flow channel 224 of the flow cell 202 in order to perform various controlled chemical reactions on the first polynucleotide 108. At least one reagent, known as an incorporation reagent, which flows over the first polynucleotide 108, includes the nucleotides 120. Each nucleotide 120 in the incorporation reagent includes a chemical tag (such as a florescent tag) which, when excited (for example by an excitation light), will emit an identification signal (such as a florescent light) which will identify the specific base of the nucleotide 120. Additionally, the base of each nucleotide 120 in the incorporation reagent includes a separable terminator, which prevents other bases from attaching to it. The chemical reactions enable the nucleotides 120 to form the base pairs 122, one base pair 122 at a time, with the sequence of bases 118 of the first polynucleotide 108.

However, if reagent exchange between the reagent flows is not sufficient, then cross contamination between reagents can occur. That is, if a first reagent is not removed and exchanged with a consecutive second reagent flow of the method, then the first reagent may contaminate the second reagent. This can lead to a phenomenon known as pre-phasing, wherein multiple tagged bases are inadvertently added to the growing complementary second polynucleotide strand with each cycle. Pre-phasing deteriorates the accuracy of the method of determining the sequence of nucleotides. Pre-phasing is also cumulative, wherein it may repeat with each cycle of the method and further reduce accuracy with each cycle. Pre-phasing will also reduce the number of bases (i.e., reduce the length) that may be built up in the complementary second polynucleotide, wherein the order of those bases may be determined within an acceptable degree of accuracy. Reagent exchange may be particularly challenging in regions of the flow cell having non-uniform channels or regions having poor fluidic flow conditions such as corners.

In addition to an increase in pre-phasing, improper reagent exchange may also contribute to other phenomenon that can deteriorate the accuracy of various methods for determining the sequence of nucleotides. For example, improper reagent exchange may lead to an increase in phasing, wherein no tagged bases are added to the growing complementary second nucleotide. Also, improper reagent exchange may lead to a decrease in percentage of clusters passing filter, which is an indication of signal purity from each cluster.

Further, when an RMS is located in a cartridge of an instrument, the reagent storage capacity of the reagent wells may be limited by the spatial constraints of the cartridge, such that efficient reagent exchange is more critical.

In the example illustrated in FIG. 2, the method has enabled tagged nucleotides 120-1 through 120-5 to sequentially combine with nucleotides 118-1 through 118-5 to form the complementary base pairs 122-1 through 122-5. Nucleotide 120-6 is the next in the sequence and is about to be combined (or paired) with nucleotide 118-6 to form the complementary base pair 122-6.

Once paired, the chemical tag of nucleotide 120-6 will be excited to emit an identification signal which will identify the base pair 122-6. Once identified, the terminator attached to the base of nucleotide 120-6 is removed so that a subsequent base may be attached. The tagged nucleotide 120-6 adds to the growing complementary second polynucleotide strand 110 that is double stranded with the first polynucleotide 108.

Accordingly, the complementary second polynucleotide strand 110 may be built up, one base 120 at a time, to determine the sequence of bases 118 in the cluster of first polynucleotides 108. The greater the number of nucleotides 120 in the complementary second polynucleotide strand 110 that can be built up (i.e., the longer the second polynucleotide stand length becomes), the more data can be provided regarding the order of nucleotides in the cluster of first polynucleotide 108 and the faster the overall analysis becomes.

Figure 3:
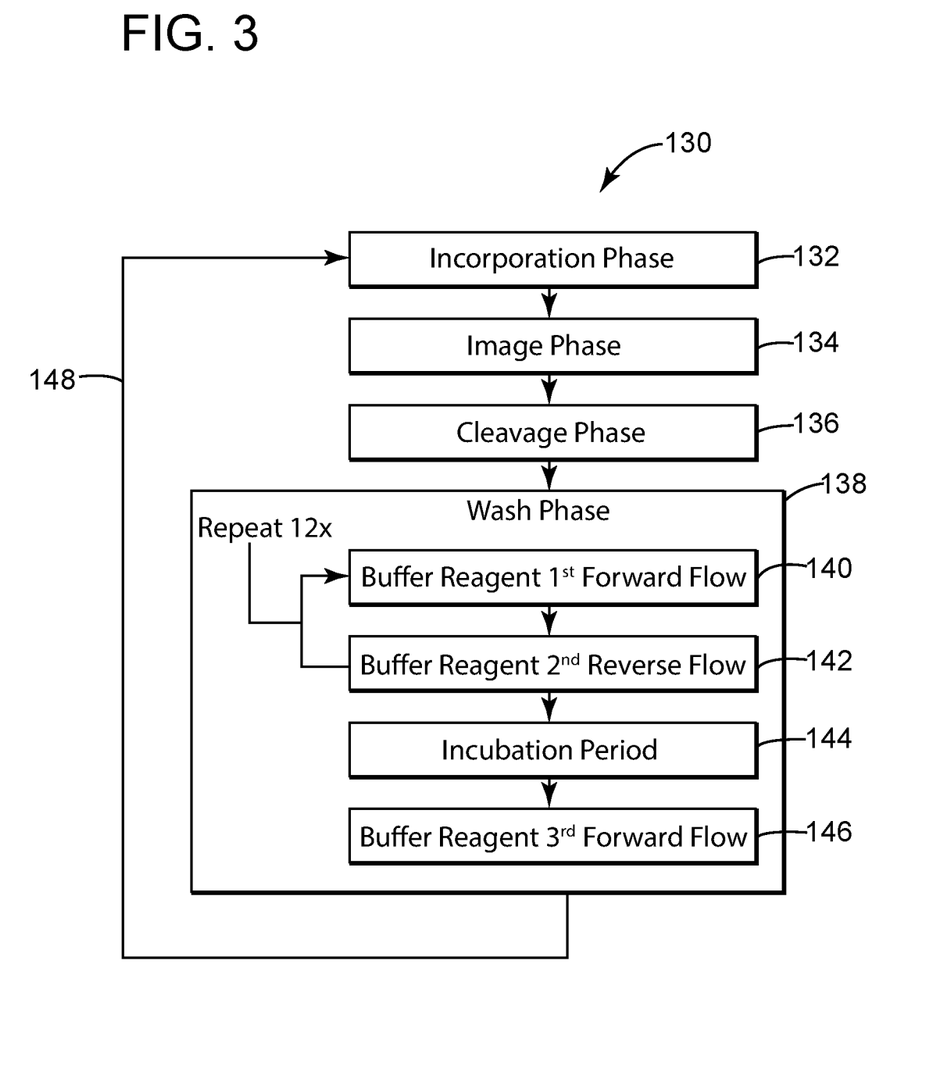
FIG. 3 depicts an example of flow diagram of a method of determining the order of nucleotides in a polynucleotide according to aspects disclosed herein.

Referring to FIG. 3 an example of a simplified flow diagram of a method 130 of determining the order of nucleotides in a polynucleotide according to aspects described herein is depicted. The method 130 includes four basic phases, which are: an incorporation phase 132, an image phase 134, a cleavage phase 136 and a wash phase 138.

During the incorporation phase 132, an incorporation reagent is flowed through a reagent management system 204 and a flow cell 202 of an instrument 200 (best seen in FIG. 7). The flow cell 202 has a first polynucleotide 108 (best seen in FIG. 2) positioned therein. The incorporation reagent adds a first base (associated with nucleotide 120-6) onto a sequence of bases (associated with nucleotides 120-1 through 120-5). The sequence of bases (and their associated nucleotides 120-1 through 120-6) include a second polynucleotide 110 that is complementary to the first polynucleotide 108.

More specifically, the incorporation reagent flows over clusters of cloned first polynucleotides 108 that are previously anchored to the flow channel 224 of the flow cell 202. The incorporation reagent includes known nucleotides 120, wherein the bases of those nucleotides 120 pair sequentially with the bases of the first polynucleotides 108 to form growing second polynucleotides 110 that are complementary to the first polynucleotide 108. The first and second polynucleotides 108, 110 form double stranded polynucleotides 112, such as DNA fragments. The types of bases of the first and second polynucleotides 108, 110 may be any one of adenine (A), guanine (G), cytosine (C), thymine (T) or uracil (U).

The nucleotides 120 in the incorporation reagent also include a tag (in this example, a florescent tag) that enables identification of the type of base with an excitation signal (in this example, with an excitation light). The nucleotides 120 also include a cleavable terminator (or blocking group) as known in the art, which prevents more than one base of the second polynucleotides 110 at a time from being paired to the bases of the first polynucleotides 108.

During the image phase 14, an image of an identification signal emanating from the first base of the nucleotide 120-6 is captured, after the first base of the nucleotide 120-6 has been added onto the second polynucleotide 110.

More specifically, the florescent tags of the nucleotides 120 associated with the second polynucleotide 110 are excited with an excitation light to emit a characteristic florescent light. An image of the florescent light is then taken to identify the base type of newly added nucleotide 120-6 in the sequence of nucleotides 120-1 through 120-6 that form the growing second polynucleotide 110. Since the second polynucleotide 110 is complementary to the first polynucleotide 108, the order of nucleotides 118 in the first polynucleotide can be determined. The longer the second polynucleotide 110 can be grown, the more of the order of nucleotides 118 in the first polynucleotide 108 can be determined.

During the cleavage phase 136, a cleavage reagent is flowed through the reagent management system 204 and flow cell 202 to remove the terminator from the nucleotide 120-6. This enables a subsequent nucleotide (not shown) in the sequence of nucleotides 120-1 through 120-6 to be added to the second polynucleotide 110.

During the wash phase 138, a buffer reagent (or wash reagent) is flowed through the reagent management system 204 and flow cell 202 in a plurality of cycles of consecutive forward and reverse flow directions to wash the cleavage reagent from the reagent management system and flow cell. The buffer reagent may be a mixture of chemicals utilized to remove unintended chemicals from the flow cell and reagent management system. The unintended chemicals may be, for example, active reagents (such as excess cleavage reagents) remaining from the previous step or various contaminants that have resulted as byproducts from the previous step. The buffer reagent may be, for example, a buffered saline solution with a lipoic acid added.

Forward flow, as used herein, refers to a direction of reagent flow from reagent wells 232 of the reagent management system 204 to the flow cell 202 (best seen in FIG. 7). Reverse flow, as used herein, refers to a direction of reagent flow from flow cell 202 to reagent wells 232.

In the example of FIG. 3, the plurality of cycles is illustrated as being 12 repetitive cycles of a forward flow direction 140 and a consecutive reverse flow direction 142 of buffer reagent. However, the buffer reagent may be cycled in a forward flow direction 140 and then in a consecutive reverse flow direction 142 any number times. For example, the plurality of cycles may be 2, 4, 6, 12 or more cycles.

The plurality of cycles of consecutive forward and reverse flow directions 140, 142 during the wash phase 138 enables a more thorough removal (i.e., reagent exchange) of cleavage reagent introduced into the system during the cleavage phase 136 than previous methods utilizing the same finite volume of buffer reagent. This is because, previous methods only flowed reagent in the forward direction during the wash phase. As such, in previous methods, the same buffer reagent would only pass through the reagent management system and flow cell once and may not sufficiently remove the cleavage reagent during the wash phase. Under those conditions, during the subsequent incorporation phase, the subsequent incorporation reagent may become contaminated with the remaining cleavage reagent. The remaining cleavage reagent may then prematurely remove the terminators from the nucleotides during the subsequent incorporation phase. This may enable an undesirable amount of pre-phasing, wherein more than one base is attached to the growing second polynucleotide at a time.

If the pre-phasing is allowed to accumulate with each new cycle, then significant uncertainty in the order of bases in the polynucleotides may develop. The uncertainty may increase over each cycle, which may decrease the accuracy of the data that can be obtained as the polynucleotide strand grows. Accordingly, the overall length of the second polynucleotide strand that can be grown, such that its order of bases can be determined with a reasonable degree of accuracy, may be limited by pre-phasing.

By comparison, the plurality of cycles of forward and reverse flow directions 140, 142 of the present disclosure enable the same buffer reagent to pass through the reagent management system and flow cell several times for a more thorough washing. In one example, employing a plurality of cycles of consecutive forward and reverse flow direction as described herein may provide for a more efficient use of the finite volume of buffer reagent, particularly where increasing the volume of buffer reagent is not desirable due to space and/or cost constraints, for example. As a result, less buffer reagent may be needed to achieve a given level of reagent exchange.

Consecutive forward and reverse flow directions 140, 142, as used herein, refers to the forward and reverse flow directions occurring adjacent to each other with no intervening steps. No intervening steps refers to no substantial incubation period (or delay time) of no flow between the reagent forward and reverse flows.

Accordingly, the flowing in a forward flow direction 140 and the flowing in a reverse flow direction 142 should be separated by a delay time of about 1 second or less, about 200 milliseconds or less, or about 100 milliseconds or less, for each cycle of the plurality of cycles of forward and reverse flow directions. Additionally, each cycle of the plurality of cycles of forward and reverse flow directions should be separated by a delay time of about 1 second or less, about 200 milliseconds or less, or about 100 millisecond or less.

In one example, in order to prevent contamination of the reagent wells 232 in the reagent management system 204 (best seen in FIG. 7), the volume of buffer reagent that flows in the forward direction 140 should be greater than the volume of buffer reagent that flows in the reverse direction. In other words, in order to prevent contamination of the reagent wells during the wash phase:

a first forward flow volume ($1^{st}$ FFV) of the buffer reagent is flowed in the forward flow direction of each cycle of the plurality of cycles; and a second reverse flow volume ($2^{nd}$ RFV) of the buffer reagent is flowed in the reverse flow direction of each cycle of the plurality of cycles, wherein the first forward flow volume is greater than the second reverse flow volume. More specifically, the first forward flow volume ($1^{st}$ FFV) may be greater than the second reverse flow volume ($2^{nd}$ RFV) by about 3% or more.

After the plurality of forward and reverse flow directions 140, 142 have taken place, the wash phase 138 proceeds to an incubation period 144. The incubation period 144 is a period of substantially no flow of buffer reagent through the reagent management system 204 and flow cell 202. The incubation period 144 may have a duration of about 10 seconds or more after the last cycle of the plurality of cycles 140, 142 has taken place.

After the incubation period 144, the wash phase 138 proceeds to a third forward flow 146. That is, a third forward flow volume ($3^{rd}$ FFV) of the buffer reagent is flowed in the forward flow direction after the incubation period 144. The incubation period 144 and third forward flow 146 may help to diffuse cleavage reagent out of cracks that may develop in the edges of the reagent management system or flow cell.

After completion of the wash phase 138, the method then cycles back 148 to the incorporation phase 132 to begin the process of adding the next nucleotide 120 in the sequence of nucleotides onto the second polynucleotide 110.

In some pre-existing methods, because the buffer reagent is only flowed in the forward direction during the wash phase, the total amount of buffer reagent consumed (the total fluidic consumption) during the wash phase is essentially equal to the total amount of buffer reagent volume that was swept through the reagent management system and flow cell (the total sweep volume) during the wash phase. By contrast, in the method of the present disclosure, the total sweep volume may be many times greater than the total fluidic consumption during the wash phase.

More specifically, total sweep volume of the buffer reagent, during the flowing the buffer reagent (wash phase), is substantially determined by the formula (($1^{st}$ FFV+$2^{nd}$ RFV)*N)+$3^{rd}$ FFV, wherein:

$1^{st}$ FFV is the first forward flow volume, $2^{nd}$ RFV is the second reverse flow volume, N is the total number of cycles in the plurality of cycles, and $3^{rd}$ FFV is the third forward flow volume.

Additionally, total fluidic consumption of the buffer reagent, during the flowing the buffer reagent (wash phase), is substantially determined by the formula:

$$(($1^{st}$ FFV-$2^{nd}$ RFV)*N)+$3^{rd}$ FFV.$$

The term "substantially determined" as used in a formula of the forgoing type is used to describe and account for measurement tolerances that may occur when determining such parameters as $1^{st}$ FFV, $2^{nd}$ RFV and $3^{rd}$ FFV.

Since the same volume of buffer reagent may pass through the reagent management system and flow cell several times, the ratio of the total sweep volume of buffer reagent to the total fluidic consumption of the buffer reagent may be substantially greater than one. More specifically, the ratio of the total sweep volume of the buffer reagent to the total fluidic consumption of the buffer reagent may be equal to or greater than about 6, about 10, about 12 or more.

In a cartridge based instrument system, the reagent management system and/or the flow cell may be positioned in a cartridge. The cartridge may be removably insertable into the instrument, meaning that the cartridge can be inserted and removed from the instrument.

As such, in a cartridge based instrument system, the large ratio (2, 6, 10, 12 or greater) of total sweep volume to total fluidic consumption may be particularly advantageous. This is because the incorporation reagent, the cleavage reagent and the buffer reagent may be stored in reagent wells of the reagent management system and the reagent management system may be part of the cartridge. Accordingly, the reagent wells of the reagent management system may be configured to store a finite total volume of each reagent in order to fit into the cartridge. The large ratio of total sweep volume to total fluidic consumption enables the same finite volume of reagent to be swept over the reagent management system and flow cell several times before it is consumed, therefore enhancing reagent exchange.

Figure 4:
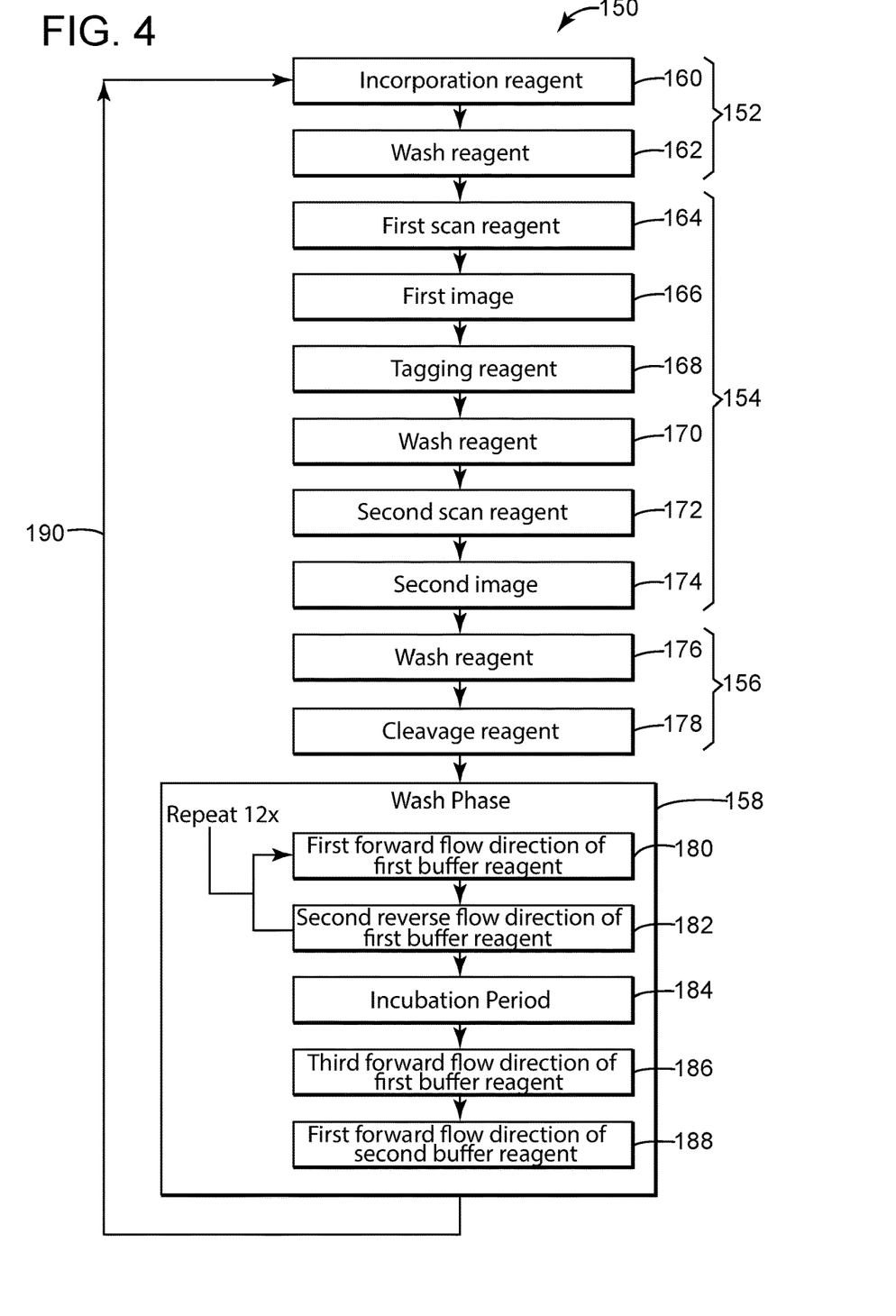
FIG. 4 depicts an example of flow diagram of another method of determining the order of nucleotides in a polynucleotide according to aspects disclosed herein.

Referring to FIG. 4, an example of flow diagram of another method 150 of determining the order of nucleotides in a polynucleotide according to aspects disclosed herein is depicted. The method 150 includes an incorporation phase 152, an image phase 154, a cleavage phase 156 and a wash phase 158.

During the incorporation phase 152, an incorporation reagent 160 is flowed through a reagent management system 204 and a flow cell 202 of an instrument 200 (best seen in FIG. 7). The incorporation reagent may be a mixture of chemicals that incorporates fluorescently-labeled nucleotides into DNA strands.

The flow cell 202 has a first polynucleotide 108 (best seen in FIG. 2) positioned therein. The incorporation reagent adds a first base (associated with nucleotide 120-6) onto a sequence of bases (associated with nucleotides 120-1 through 120-5). The sequence of bases (and their associated nucleotides 120-1 through 120-6) form a second polynucleotide 110 that is complementary to the first polynucleotide 108.

The nucleotides 120 in the incorporation reagent also include a tag (in this example, a florescent tag) that enables identification of the type of base with an excitation signal (in this example, with an excitation light). The nucleotides 120 also include a cleavable terminator (or blocking group) as known in the art, which prevents more than one base of the second polynucleotides 110 at a time from being paired to the bases of the first polynucleotides 108.

Next during the incorporation phase 152, a wash reagent 162 is used to remove any excess incorporation reagent 160. The wash reagent may be a mixture of chemicals utilized to remove the active reagents from a flow cell.

The method proceeds to the image phase 154, wherein a scan reagent 164 is used to protect the flow cell surface from photo damage prior to an image being taken. The scan reagent 164 may be a mixture of chemicals that stabilize nucleotide strands during a detection process.

Next during the image phase 154, an image of an identification signal emanating from the first base of the nucleotide 120-6 is captured 166, after the first base of the nucleotide 120-6 has been added onto the second polynucleotide 110.

More specifically, the florescent tags of the nucleotides 120 associated with the second polynucleotide 110 are excited with an excitation light to emit a characteristic florescent light. An image of the florescent light is then taken to provide identification information on the base type of newly added nucleotide 120-6 in the sequence of nucleotides 120-1 through 120-6 that form the growing second polynucleotide 110.

Next during the image phase 154, an additional tagging reagent 168 is used to attach a second tag to the newly added nucleotide 120-6. The tagging reagent 168 may be a mixture of chemicals utilized to deliver a florescent tag to the nucleotide.

Next during the image phase 154, a wash reagent 170 is used to remove the excess tagging reagent 168. The wash reagent 170 may be a mixture of chemicals utilized to remove the active reagents from a flow cell.

Next during the image phase 154, a second scan reagent 172 is applied to protect the flow cell surface from photo damage prior to a second image being taken. The second scan reagent may be a mixture of chemicals that stabilize nucleotide strands during a detection process.

Next during the image phase 154, a second image of a second identification signal emanating from the first base of the nucleotide 120-6 is captured 174. More specifically, the florescent second tags of the nucleotides 120 associated with the second polynucleotide 110 are excited with an excitation light to emit a characteristic second florescent light. An image of the second florescent light is then taken to provide additional identification information on the base type of newly added nucleotide 120-6.

The method proceeds to the cleavage phase 156, wherein a wash reagent 176 is used to remove any excess second scan reagent 172. The wash reagent may be a mixture of chemicals utilized to remove the active reagents from a flow cell.

Next during the cleavage phase 156, a cleavage reagent 178 is flowed through the reagent management system 204 and flow cell 202 to remove the terminator from the nucleotide 120-6. This enables a subsequent nucleotide (not shown) in the sequence of nucleotides 120-1 through 120-6 to be added to the second polynucleotide 110.

The method proceeds to the wash phase 158, wherein a first buffer reagent is flowed through the reagent management system 204 and flow cell 202 in a plurality of cycles of consecutive forward and reverse flow directions to wash the cleavage reagent 178 from the reagent management system and flow cell. The first buffer reagent may be, for example, a buffered saline solution with a lipoic acid added.

More specifically, a first forward flow volume ($1^{st}$ FFV) of 22 microliters (µL) of the first buffer reagent is flowed in the forward flow direction 180 to begin each cycle of the plurality of cycles. A second reverse flow volume ($2^{nd}$ RFV) of 19 microliters (µL) of the first buffer reagent is then flowed in the reverse flow direction 182 to end each cycle of the plurality of cycles. In this specific example of FIG. 4, there are a total of 12 cycles of forward and reverse flows.

Next during the wash phase 158, an incubation period 184 of substantially no flow of first buffer reagent through the reagent management system 204 and flow cell 202 is imposed on the system. The incubation period 184 in this specific example has a duration of about 30 seconds, though other incubation periods may be used.

After the incubation period 184, the wash phase 158 proceeds to a third forward flow 186. That is, a third forward flow volume ($3^{rd}$ FFV) of 12 microliters (µL) of the first buffer reagent is flowed in the forward flow direction after the incubation period 184.

The first buffer reagent is utilized in the wash phase 158 to substantially remove the cleavage reagent 178 from the system. However, specific chemicals in the first buffer reagent that are effective in removing the cleavage reagent 178, may also interfere with the incorporation reagent of the next cycle. One such example of such a chemical may be lipoic acid.

Accordingly, during the wash phase 158, a forward flow of a second buffer reagent 188 is flowed through the reagent management system and flow cell to remove the first buffer reagent. The second buffer reagent may be a saline solution without lipoic acid. The second buffer reagent is not important in the removal of the cleave agent, but will not interfere with the incorporation reagent 160 on the next cycle.

After completion of the wash phase 158, the method then cycles back 190 to the incorporation phase 152 to begin the process of adding the next nucleotide 120 in the sequence of nucleotides onto the second polynucleotide 110.

As stated previously herein, the total sweep volume of the first buffer reagent, during the wash phase, is substantially determined by the formula $((1^{st}\,FFV+2^{nd}\,RFV)*N)+3^{rd}\,FFV$, wherein:

$1^{st}$ FFV is the first forward flow volume and is equal to 22 µL, $2^{nd}$ RFV is the second reverse flow volume and is equal to 19 µL, N is the total number of cycles in the plurality of cycles and is equal to 12, and $3^{rd}$ FFV is the third forward flow volume and is equal to 12 µL.

Accordingly, in the example of FIG. 4, the total sweep volume is equal to $$(22+19)*12+12=504\,\mu L.$$

Additionally, total fluidic consumption of the first buffer reagent, during the wash phase, is substantially determined by the formula:

$$(1^{st}\,FFV-2^{nd}\,RFV)*N+3^{rd}\,FFV.$$

Accordingly, in the example of FIG. 4, the total fluidic consumption is equal to:

$$(22-19)*12+12=48\,\mu L.$$

Additionally, in the example of FIG. 4, the ratio of total sweep volume to total fluidic consumption is equal to: 504/48=10.5. By way of comparison, the ratio of total sweep volume to total fluidic consumption of previous systems is essentially 1. This is because, previous systems only utilize a forward flow of buffer reagent that is effective in the removal of cleavage reagent.

Figure 5:
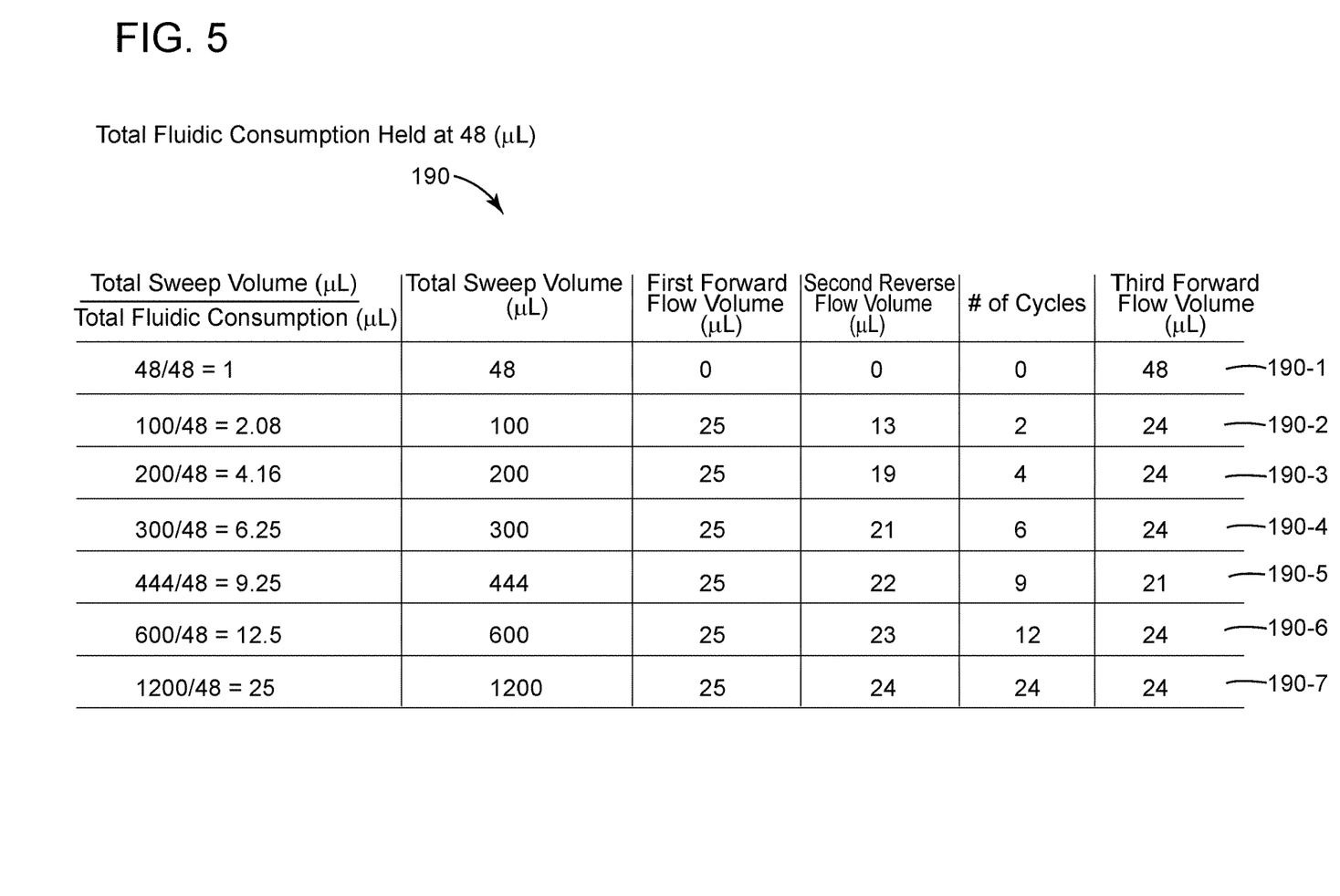
FIG. 5 depicts a table showing various ratios of total sweep volume to total fluidic consumption of buffer reagent obtained during a working example of a wash phase according to aspects disclosed herein.
Figure 6:
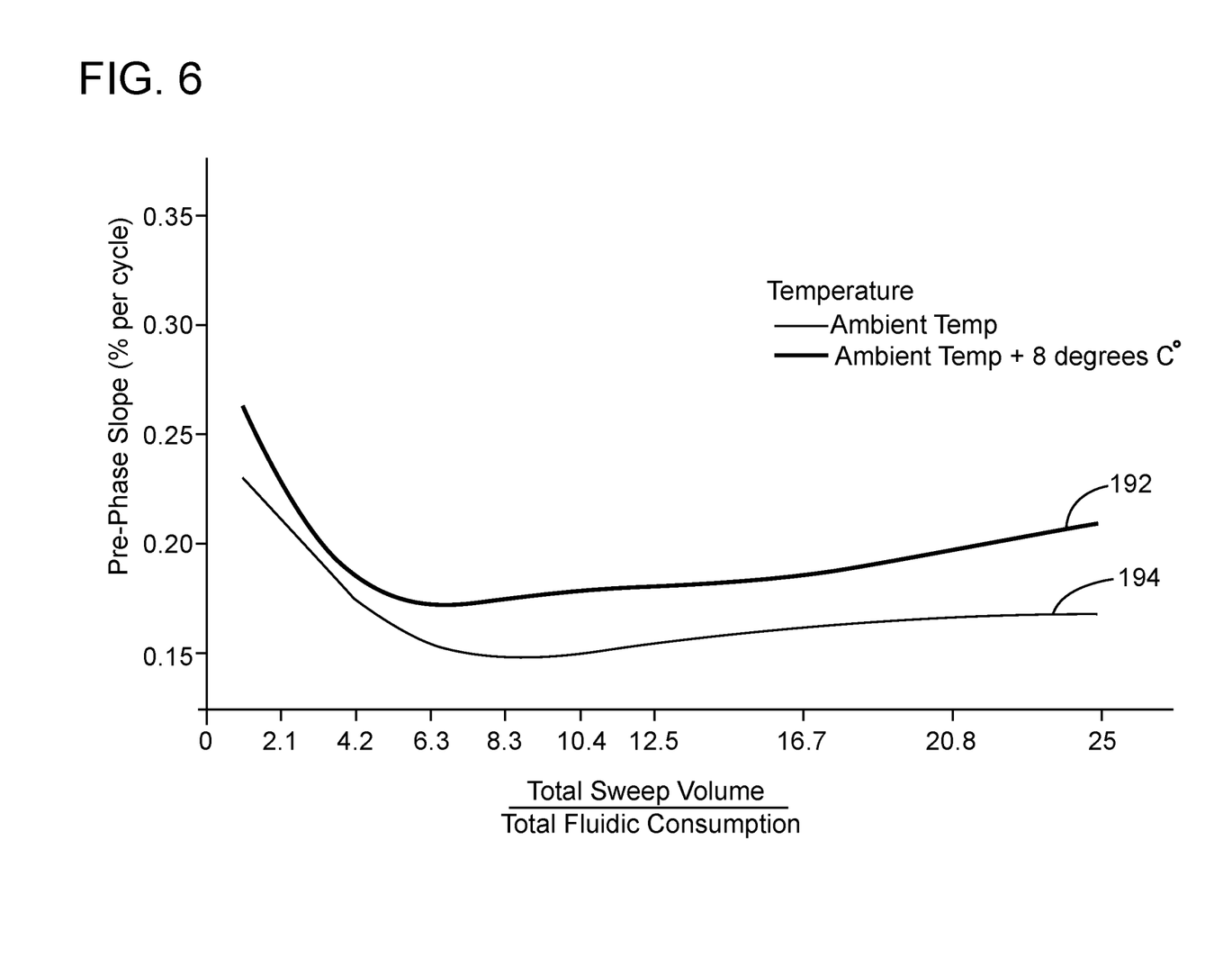
FIG. 6 depicts graphs of ratios of total sweep volumes to total fluidic consumption vs. pre-phasing slope that were plotted from the data obtained in the working example of FIG. 5 according to aspects disclosed herein.

FIGS. 5 and 6 show results obtained from a non-limiting working example.

Referring to FIG. 5, a table 190 showing a working example of various ratios of total sweep volume to total fluidic consumption of the first buffer reagent that were obtained during an example wash phase 158 of method 150 is depicted. In rows 190-1 through 190-7, the total fluidic consumption was held constant at 48 µL. Also in rows 190-2 through 190-7, the first forward flow volume ($1^{st}$ FFV), second reverse flow volume ($2^{nd}$ RFV), number of cycles (N) and third forward flow volume ($3^{rd}$ FFV) were varied to increase the total sweep volume from 100 µL to 1200 µL, while the total fluidic consumption was held constant at 48 µL. As can be seen, the ratio of total sweep volume to total fluidic consumption varied from 2.08 (in row 190-2) to 25 (in 190-7).

The top row 190-1 represents a comparative example of a previous method, wherein there was no cycling of reverse and forward flows of buffer reagent. Rather, row 190-1 had only a forward flow during the wash phase and, therefore, its total sweep volume was equal to its total fluidic consumption.

Referring to FIG. 6, graphs 192, 194 of ratios of total sweep volumes to total fluidic consumption vs. pre-phasing slope that were plotted from the data obtained in the working example of FIG. 5 according to aspects disclosed herein are depicted. Graph 194 was plotted at an ambient temperature (for example at an ambient temperature within a range of 25 to 35 degrees centigrade). Graph 192 was plotted at the ambient temperature plus 8 degrees centigrade (for example at a temperature within a range of 33 to 43 degrees centigrade).

Pre-phasing slope, as indicated in graphs 192 and 194, is expressed as the percentage (%) of molecules in clusters of polynucleotides in a flow cell that are leading by 1 base pair per cycle. Pre-phasing slope is a measure of the rate of pre-phasing per cycle.

The lower the pre-phasing values, the better the data quality is at a given polynucleotide length during the processing of the methods herein. Additionally, the lower the pre-phasing values, the longer the polynucleotides that can be grown.

As can be determined from graphs 192 and 194, an optimal range for the ratio of total sweep volume to total fluidic consumption, wherein the lowest pre-phasing slope percentage can be achieved, is equal to or greater than about 6. An alternative optimal range, that can be determined from the graphs 192, 194 of the plotted data of the working example of FIG. 5, would also be from about 6 to about 12.

The optimal ranges are associated with low pre-phase slopes. In most cases in the working example of FIG. 6, the optimal ranges are associated with pre-phase slope percentages that are below 2.0%. Such low pre-phase slope percentages provided the surprising results, obtained from the working example of FIGS. 5 and 6, of enabling a complementary second polynucleotide 110 to be built up to longer lengths of bases than previously obtained with a finite amount of reagent, within an acceptable accuracy. In the working example of FIGS. 5 and 6, cartridge based instrument systems were be able to accurately build the second complementary polynucleotides 110 up to lengths of 200 bases or more a high percentage of time (e.g., above 90% of the time). Therefore, the base pairs of the first and second polynucleotides 108, 110 were also able to be accurately built up to lengths of 200 base pairs or more that same high percentage of time.

Referring to FIG. 7, an example of a schematic diagram of an instrument 200 according to aspects described herein is depicted. The instrument, in this particular example, includes a cartridge 230 engaged therein. The cartridge 230 includes a flow cell 202 in fluid communication with a reagent management system (RMS) 204. In this particular example, the RMS 204 is in fluid communication with the flow cell 202 through an intermediate connection 206. The cartridge 230 may be removably insertable into the instrument 200, meaning that the cartridge can be inserted and removed from the instrument.

Even though the example of this FIG. 7 illustrates a cartridge-based instrument 200 having an RMS 204 and flow cell 202 contained in a cartridge 230, other instruments 200 may not include such a cartridge-based system. Rather, in some instruments 200, the components of the RMS 204 may be integrally and rigidly mounted within the instrument 200, and only the flow cell 202 may be detachable from the instrument 200. Still further, the flow cell 202 may, or may not, be detachable from the cartridge 230.

The RMS includes a plurality of reagent wells 232. Each reagent well 232 is operable to contain a reagent of a plurality of reagents 208-218 positioned therein. The RMS 204 is operable to select a flow of reagent 234 from one of the plurality of reagents 208-218.

The RMS is also operable to direct the flow of reagent 234 in the forward direction and the reverse direction. Forward flow, as used herein, refers to the direction of reagent flow 234 from the reagent wells 232 to the flow cell 202. Reverse flow, as used herein, refers to the direction of reagent flow 234 from flow cell 202 to reagent wells 232.

The reagents 208-218 may be any of several types or combinations of reagents depending on the type and sequence of the chemical reactions that are to be performed at the flow cell. For example, the reagents 208-218 may be of the following types:

Reagent 208 and 209 may be different formulations of an incorporation reagent.
Reagent 210 and 211 may be different formulations of a scan reagent.
Reagent 212 may be a cleavage reagent.
Reagent 214 and 216 may be different formulations of a buffer reagent.
Reagent 218 may be air.

The connection 206 includes a first channel 236 in fluid communication with the RMS 204 through an RMS outlet port 256. The first channel 236 is operable to route the flow of reagent 234 through an inlet port 220 of the flow cell 202 and into the flow channel 224 of the flow cell 202. The connection 206 also includes a second channel 238 in fluid communication with the flow channel 224 through an outlet port 222 of the flow cell 202. The second channel 238 is operable to route the flow of reagent 234 from the flow cell 202, through an RMS inlet port 258 and back into the RMS 204 after the flow of reagent 234 has passed through the flow channel 224.

The flow cell 202 of the instrument 200 includes the flow channel 224 in fluid communication with the first channel 236 through the inlet port 220, and in fluid communication with the second channel 238 through the outlet port 222. The flow channel 224 is operable to perform a variety of chemical reactions between the various flows of reagent 234 from the plurality of reagents 208-218 and polynucleotides, such as polynucleotides 108 of FIG. 2, positioned in the flow channel 224.

Though the example of FIG. 7 illustrates a flow cell 202 with a single inlet port 220 and a single outlet port 222, other configurations of flow cells may also be utilized. For example, the flow cell 202 may include multiple inlet ports 220 for receiving reagent flows from multiple channels of the connection 206. Also, by way of example, the flow cell may include multiple outlet ports 222 for routing reagent flow to multiple channels of the connection 206.

Though the example of FIG. 7 illustrates the flow cell 202 in fluid communication with the RMS 204 though an intermediate connection 206, the flow cell 202 may alternatively be directly connected to the RMS 204 without a connection 206 therebetween. That is, the RMS outlet port 256 may be directly connected to the flow cell inlet port 220 and the RMS inlet port 258 may be directly connected to the flow cell outlet port 222.

The RMS 204, in this example, includes a rotary valve 242 for selecting the reagents 208-218. The rotary valve 242 has an internal rotary valve body 244. The valve body 244 includes a center port 246 and a rotatable port 248, which are connected by a rotary channel 250. The valve body 244 pivots around the center port 246 to move the rotatable port 248.

The plurality of reagent wells 232, which contain the reagents 208-218, may be disposed around the periphery of the rotary valve 242 or otherwise remote from the rotary valve 242. Each reagent well 232 is in fluid communication with a corresponding well channel 252. Each well channel 252 includes a well channel port 254 that the rotatable port 248 of the rotary valve 242 may align with in order to receive the flow of reagent 234 from any given reagent well 232.

When the rotatable port 248 aligns with one of the well channel ports 254, a flow path for a flow of reagent 234 is established that allows the flow of reagent 234 to flow from the selected well 232, through the well channel 252, through the rotary valve 242, through a common line 255 and out the RMS outlet port 256. The flow of reagent 234 then continues through the first channel 236, into the inlet port 220 of the flow cell 202 and through the flow channel 224, where the selected reagent of the plurality of reagents 208-218 may react with the polynucleotides 108.

The unreacted reagents and/or by products of the reaction may flow out the outlet port 222 of the flow cell 202 and through the second channel 238. The reagent flow 234 may then re-enter the RMS 204 through the RMS inlet port 258.

The RMS inlet port 258 of the RMS 204 is in fluid communication with a first pinch valve 260. The first pinch valve 260 is in fluid communication with a second pinch valve 262. The first and second pinch valves 260, 262 include a resilient central portion that may be mechanically or pneumatically actuated to pinch off or release the flow of reagent 234 through the pinch valves 260, 262. Additionally, though pinch valves 260, 262 are illustrated in this example, other types of valves may be utilized to perform the same function. For example, the valves 260, 262 may be rotary valves.

An onboard pump 264 (such as a syringe pump, or similar) is also disposed on the RMS 204. Even though the onboard pump 264 may be other types of pumps, it will be referred to herein as the syringe pump 264. The syringe pump 264 is connected in a tee formation between the first and second pinch valves 260, 262. Both pinch valves 260, 262 are opened and closed by the instrument 200 to engage or disengage the syringe pump 264 from the flow cell 202 and/or a waste tank 270.

The syringe pump 264 includes a reciprocating plunger 266 disposed in a cylinder 268, which has a cylinder bore 270. The plunger 266 is received within the cylinder bore 270 to form a plunger-cylinder bore seal. The plunger 266 is driven by the instrument 200 to reciprocate within the cylinder bore 270 and to pump the reagents 208-218 in a forward flow direction from the reagent wells 232 to the waste tank 272.

In addition to the instrument 200 being operable to pump the flow of reagents 234 in a forward direction from reagent wells 232 to the flow cell 202 and onto to the pump 264, the instrument 200 may be operable to pump the flow of reagents 234 in the reverse direction. That is, the reagents 208-218 may be pumped in a reverse flow direction from the pump 264 to the flow cell 202 and onto the reagent wells 232. Accordingly, the instrument is operable to, for example, flow buffer reagents 214, 216 through the RMS 204 and flow cell 202 in a plurality of cycles of consecutive forward and reverse flow directions in accordance with methods 130 of FIG. 3 and 150 of FIG. 4.

The instrument 200 also includes the detection module 226, which is operable to detect photons of light, or other forms of detectable properties, when a chemical reaction caused by the reagents 208-218 induces the polynucleotides 108 to affect such detectable properties.

Though the implementation illustrated in FIG. 7 is that of an instrument 200 utilizing a rotary valve 242 that routes the various reagents 208-218 through a common line 255 and into the flow cell 202, other instruments 200 may not utilize a rotary valve 242. For example, the well channels 252 from each reagent well 232 may extend directly to one of a plurality of separate RMS outlet ports 256.

In that case, the well channels 252 may each include a valve (not shown) to control the reagent flow 234 from each reagent well 232. Additionally, the first channel 236 may be a plurality of first channels to each receive the corresponding flow of reagent 234 from a corresponding RMS outlet port 256. Moreover, the inlet port 220 of the flow cell 202 may be a plurality of inlet ports 220 to receive the various reagent flows 234 from each of the plurality of first channels 236.

Figure 8:
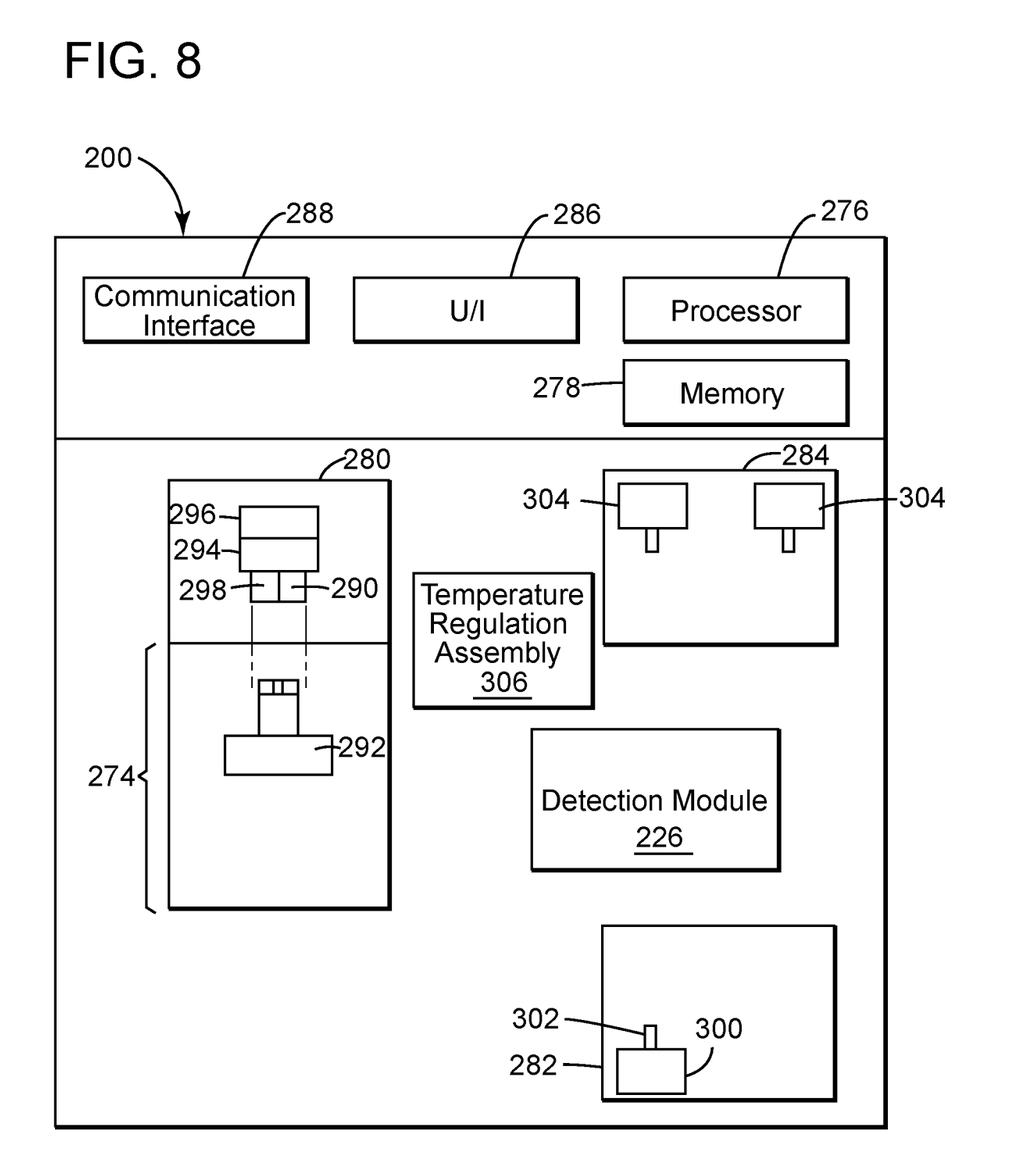
FIG. 8 depicts an example of a schematic block diagram of the instrument of FIG. 7 according to aspects disclosed herein.

Referring to FIG. 8, an example of a schematic block diagram of the instrument 200 of FIG. 7 is depicted. The instrument 200 includes a docking station 274 to receive the cartridge 230. Various electrical and mechanical assemblies within the instrument 200 interact with the cartridge 230 to operate the cartridge during a microfluidics analysis operation of the various chemical reactions that are performed in the flow cell 202.

The instrument 200 may include, among other things, one or more processors 276 that are to execute program instructions stored in a memory 278 in order to perform the microfluidics analysis operations. The processors are in electronic communication to a rotary valve drive assembly 280, a syringe pump drive assembly 282, a pinch valve drive assembly 284, the detection module 226 and a temperature regulation assembly 306.

A user interface 286 is provided for users to control and monitor operation of the instrument 200. A communications interface 288 can convey data and other information between the instrument 200 and remote computers, networks and the like.

The rotary valve drive assembly 280 includes a drive shaft 290, which is mechanically coupled to a rotary valve interface bracket 292. The rotary valve interface bracket 292 is selectively mechanically coupled to the rotary valve 242 of the cartridge 230. The rotary valve drive assembly 280 includes a rotation motor 294 and, in some implementations, a translation motor 296. The translation motor 296 can move the drive shaft 290 in a translational direction between an engaged state and a disengaged state with the rotary valve 242. The rotary motor 294 manages rotation of the rotary valve body 244 of the rotary valve 242.

The rotary valve drive assembly 280 also includes a position encoder 298 that monitors the position of the drive shaft 290. The encoder 298 provides position data to the processor 276.

The syringe pump drive assembly 282 includes a syringe pump motor 300 coupled to an extendable shaft 302. The shaft 302 is driven by the syringe pump motor 300 between an extended position and a retracted position to reciprocate the plunger 366 within the cylinder bore 270 of the cylinder 268 on the syringe pump 264.

The pinch valve drive assembly 284 includes a set of two pneumatically driven pinch valve drive motors 304. The two pinch valve drive motors 304 are mechanically coupled to a corresponding one of the first and second pinch valves 260, 262. The pinch valve drive motors 304 may utilize air pressure to pinch off or release a resilient central portion of the first and/or second pinch valves 260, 262 to pneumatically open and close the first and/or second pinch valves 260, 262. Alternatively, the pinch valve drive motors 304 may be electrically driven.

The detection module 226 may contain all of the cameras and/or detecting sensors suitable and/or needed to enable the detection of emissive light photons, or other forms of detectable properties, related to polynucleotides 108 in the flow cell 202. Device circuitry (not shown) within the instrument 200 may then process and transmit data signals derived from those detected emissions. The data signals may then be analyzed to reveal properties of the polynucleotides 108.

A temperature regulation assembly 306 (or other environmental control device) may also be included in the instrument 200. The temperature regulation assembly 306 may be utilized to provide temperature control of the flow cell 202 during the various chemical reactions. More specifically, the temperature regulation assembly 306 may provide both heating and cooling of the flow cell 202, thereby enabling thermocycling of the flow cell 202. An environmental control device may control or regulate parameters other than just temperature (e.g., pressure).

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the forgoing disclosure has been described by reference to specific examples, it should be understood that numerous changes may be made within the spirit and scope of the inventive concepts described. Accordingly, it is intended that the disclosure is not be limited to the described examples, but that it has the full scope defined by the language of the following claims.

What is claimed is:

1. A method, comprising:
    flowing an incorporation reagent, through a reagent management system and a flow cell of an instrument, the flow cell having a first polynucleotide positioned therein, wherein the incorporation reagent adds a first base onto a sequence of bases, the sequence of bases comprising a second polynucleotide complementary to the first polynucleotide;
    capturing an image, of an identification signal emanating from the first base, after the first base has been added onto the second polynucleotide;
    flowing a cleavage reagent, through the reagent management system and flow cell, to remove a first terminator from the first base in order to enable a subsequent base in the sequence of bases to be added to the second polynucleotide; and
    flowing a buffer reagent, through the reagent management system and flow cell in a plurality of cycles of consecutive forward and reverse flow directions to remove the cleavage reagent from the flow cell.

2. The method of claim 1, wherein the plurality of cycles comprises 4 or more cycles.

3. The method of claim 1, wherein the plurality of cycles comprises 12 or more cycles.

4. The method of claim 1, wherein the reagent management system and the flow cell are positioned in a cartridge of the instrument, the cartridge being removably insertable into the instrument.

5. The method of claim 1, wherein the incorporation reagent, the cleavage reagent and the buffer reagent are stored in reagent wells of the reagent management system, the reagent wells operable to store a finite total volume of each reagent.

6. The method of claim 1, wherein flowing the buffer reagent comprises:

flowing a first forward flow volume of the buffer reagent in the forward flow direction of each cycle of the plurality of cycles; and flowing a second reverse flow volume of the buffer reagent in the reverse flow direction of each cycle of the plurality of cycles, the first forward flow volume being greater than the second reverse flow volume.

7. The method of claim 6, wherein the forward flow volume is greater than the reverse flow volume by about 3% or more.

8. The method of claim 6, wherein the flowing the buffer reagent comprises:

an incubation period of substantially no flow of buffer reagent through the reagent management system and flow cell for about 10 seconds or more after the last cycle of the plurality of cycles; and flowing a third forward flow volume of the buffer reagent in the forward flow direction after the incubation period.

9. The method of claim 8, wherein total sweep volume of the buffer reagent, during the flowing the buffer reagent, is substantially determined by the formula $((1^{st} FFV + 2^{nd} RFV)*N) + 3^{rd} FFV$, wherein:

$1^{st}$ FFV is the first forward flow volume, $2^{nd}$ RFV is the second reverse flow volume, N is the total number of cycles in the plurality of cycles, and $3^{rd}$ FFV is the third forward flow volume.

10. The method of claim 9, wherein total fluidic consumption of the buffer reagent, during the flowing the buffer reagent, is substantially determined by the formula $((1^{st} FFV - 2^{nd} RFV)*N) + 3^{rd} FFV$.

11. The method of claim 10 wherein the ratio of the total sweep volume of the buffer reagent to the total fluidic consumption of the buffer reagent is equal to or greater than about 6.

12. The method of claim 11, wherein each cycle of the plurality of cycles of forward and reverse flow directions is separated by a delay time of about 200 milliseconds or less.

13. The method of claim 1, wherein the flowing in a forward flow direction and the flowing in a reverse flow direction are separated by a delay time of about 1 second or less for each cycle of the plurality of cycles of forward and reverse flow directions.

14. The method of claim 1, wherein the flowing in a forward flow direction and flowing in a reverse flow direction is separated by a delay time of about 200 milliseconds or less for each cycle of the plurality of cycles of forward and reverse flow directions.

15. An instrument comprising:

a reagent management system, positioned in the instrument, the reagent management system comprising a plurality of reagent wells, the reagent wells having at least a first, a second and a third reagent well operable to contain an incorporation reagent, a cleavage reagent and a buffer reagent positioned respectively therein, the reagent management system to select a flow of reagent from one of the plurality of reagent wells; and a flow cell, positioned in the instrument, the flow cell comprising a flow channel in fluid communication with the reagent management system, the flow channel to route the flow of reagent over a first polynucleotide positioned in the flow channel;

wherein the instrument is operable to:

flow the incorporation reagent, through the reagent management system and flow cell, to add a first base onto a sequence of bases, the sequence of bases comprising a second polynucleotide complementary to the first polynucleotide;

capture an image, of an identification signal emanating from the first base, after the first base has been added onto the second polynucleotide;

flow the cleavage reagent, through the reagent management system and flow cell, to remove a first terminator from the first base in order to enable a subsequent base in the sequence of bases to be added to the second polynucleotide; and flow the buffer reagent, through the reagent management system and flow cell in a plurality of cycles of consecutive forward and reverse flow directions to remove the cleavage reagent from the flow cell.

16. The instrument of claim 15, comprising:

a cartridge to contain the reagent management system and the flow cell;

wherein the incorporation reagent, the cleavage reagent and the buffer reagent are stored in reagent wells of the reagent management system, the reagent wells store a finite total volume of each reagent.

17. The instrument of claim 15, wherein, the instrument is operable to flow the buffer reagent through the reagent management system and flow cell in a plurality of 4 or more cycles of consecutive forward and reverse flow directions.

18. The instrument of claim 15, wherein, the instrument is operable to flow the buffer reagent such that:

a first volume of the buffer reagent is flowed in the forward flow direction of each cycle of the plurality of cycles;

a second volume of the buffer reagent is flowed in the reverse flow direction of each cycle of the plurality of cycles, the first volume being greater than the second volume;

an incubation period of substantially no flow of the buffer reagent through the reagent management system and flow cell is imposed for about 10 seconds or more after the last cycle of the plurality of cycles; and a third forward flow volume of the buffer reagent is flowed in the forward flow direction after the incubation period.

19. The instrument of claim 18 wherein, the instrument is operable to flow the buffer reagent such that:

a total sweep volume of the buffer reagent is substantially determined by the formula $((1^{st} FFV + 2^{nd} RFV)*N) + 3^{rd} FFV$, wherein:

$1^{st}$ FFV is the first forward flow volume, $2^{nd}$ RFV is the second reverse flow volume, N is the total number of cycles in the plurality of cycles, and $3^{rd}$ FFV is the third forward flow volume;

a total fluidic consumption of the buffer reagent is substantially determined by the formula $((1^{st} FFV - 2^{nd} RFV)*N) + 3^{rd} FFV$; and wherein the ratio of the total sweep volume of the buffer reagent to the total fluidic consumption of the buffer reagent is equal to or greater than about 6.

20. The instrument of claim 18, wherein the instrument is operable to flow the buffer reagent such that the flowing in a forward flow direction and flowing in a reverse flow direction is separated by a delay time of about 200 millisecond or less for each cycle of the plurality of cycles of forward and reverse flow directions.

* * * * *